United States Patent
Miller et al.

(10) Patent No.: US 9,421,341 B2
(45) Date of Patent: Aug. 23, 2016

(54) LARYNGEAL TUBE

(75) Inventors: David J. Miller, Pittsburg, KS (US);
Thomas W. McGrail, Cicero, IN (US);
Benje Boedeker, Omaha, NE (US);
Volker Bertram, Sulz am Neckar (DE)

(73) Assignee: King Systems Corporation,
Noblesville, IN (US)

( * ) Notice: Subject to any disclaimer, the term of this patent is extended or adjusted under 35 U.S.C. 154(b) by 896 days.

(21) Appl. No.: 13/580,978

(22) PCT Filed: Feb. 26, 2011

(86) PCT No.: PCT/US2011/026392
§ 371 (c)(1),
(2), (4) Date: Nov. 1, 2012

(87) PCT Pub. No.: WO2011/106754
PCT Pub. Date: Sep. 1, 2011

(65) Prior Publication Data
US 2013/0056003 A1   Mar. 7, 2013

Related U.S. Application Data

(60) Provisional application No. 61/308,898, filed on Feb. 27, 2010.

(51) Int. Cl.
*A61M 16/04* (2006.01)
*A61M 16/00* (2006.01)

(52) U.S. Cl.
CPC ....... *A61M 16/0463* (2013.01); *A61M 16/0479* (2014.02); *A61M 16/0484* (2014.02); *A61M 16/0486* (2014.02); *A61M 16/0434* (2013.01); *A61M 2016/0027* (2013.01); *A61M 2205/18* (2013.01); *A61M 2205/44* (2013.01); *A61M 2205/581* (2013.01); *A61M 2205/584* (2013.01)

(58) Field of Classification Search
CPC ............ A61M 16/04; A61M 16/0409; A61M 16/0411; A61M 16/0434; A61M 16/0459; A61M 16/0475; A61M 16/0477; A61M 16/0479; A61M 16/0488; A61M 16/0493; A61M 16/0495; A61M 16/0497; A61M 16/0486; A61M 2210/0656; A61B 1/267
See application file for complete search history.

(56) References Cited

U.S. PATENT DOCUMENTS 4,230,108 A * 10/1980 Young .................... 128/207.15
4,244,362 A    1/1981 Anderson
(Continued)

FOREIGN PATENT DOCUMENTS

WO    WO/2006081326    8/2006

OTHER PUBLICATIONS

Written Opinion of the International Search Authority in PCT/US2011/26392, Aug. 2012, 4 pgs.

*Primary Examiner* — Justine Yu
*Assistant Examiner* — Michael Tsai
(74) *Attorney, Agent, or Firm* — Faegre Baker Daniels LLP

(57) ABSTRACT

A laryngeal tube comprising a tubular component and a nozzle having a central cavity, an anterior opening and a tongue at least partially covering the central cavity. In one example, the laryngeal tube has a first lumen to deliver gases to a patient and a fluid barrier supported by the nozzle. In other examples, the laryngeal tube may include additional lumens including a service lumen to perform a function associated with the thorax and an inflation lumen to inflate the fluid barrier.

22 Claims, 15 Drawing Sheets

(56) References Cited

U.S. PATENT DOCUMENTS

| | | | |
|---|---|---|---|
| 4,338,930 | A | 7/1982 | Williams |
| 4,612,927 | A | 9/1986 | Kruger |
| 4,637,389 | A | 1/1987 | Heyden |
| 4,737,147 | A | 4/1988 | Ferrando et al. |
| 4,919,126 | A | 4/1990 | Baildon |
| 5,038,761 | A | 8/1991 | Richardson |
| 5,038,766 | A | 8/1991 | Parket |
| 5,285,778 | A | 2/1994 | Mackin |
| 5,287,848 | A | 2/1994 | Cubb et al. |
| 5,303,697 | A | 4/1994 | Brain |
| 5,499,625 | A | 3/1996 | Frass et al. |
| 5,720,275 | A | 2/1998 | Patil et al. |
| 5,765,559 | A | 6/1998 | Kim |
| 5,819,733 | A | 10/1998 | Bertram |
| 5,840,013 | A | 11/1998 | Lee et al. |
| 5,865,176 | A * | 2/1999 | O'Neil .................... 128/207.15 |
| 5,896,858 | A | 4/1999 | Brain |
| 5,921,917 | A | 7/1999 | Barthel et al. |
| 5,937,859 | A | 8/1999 | Augustine et al. |
| 5,941,816 | A | 8/1999 | Barthel et al. |
| 6,079,409 | A | 6/2000 | Brain |
| 6,390,093 | B1 * | 5/2002 | Mongeon ................ 128/207.15 |
| 6,568,388 | B2 | 5/2003 | Christopher |
| 6,609,521 | B1 | 8/2003 | Belani et al. |
| 6,843,250 | B2 | 1/2005 | Efrati |
| 6,843,769 | B1 | 1/2005 | Gandarias |
| 6,918,388 | B2 | 7/2005 | Brain |
| 6,983,744 | B2 | 1/2006 | Alfery |
| 7,040,322 | B2 * | 5/2006 | Fortuna .................. 128/207.15 |
| 7,096,868 | B2 | 8/2006 | Tateo et al. |
| 7,097,802 | B2 | 8/2006 | Brain |
| 7,121,280 | B2 * | 10/2006 | Kyle, Jr. ................. 128/207.14 |
| 7,128,071 | B2 | 10/2006 | Brain |
| 7,159,589 | B2 | 1/2007 | Brain |
| 7,201,168 | B2 | 4/2007 | McGrail |
| 7,263,998 | B2 | 9/2007 | Miller |
| 7,305,985 | B2 | 12/2007 | Brain |
| 7,331,346 | B2 | 2/2008 | Zocca et al. |
| 7,360,540 | B2 | 4/2008 | Brain et al. |
| 7,543,586 | B2 | 6/2009 | Qureshi et al. |
| 7,654,264 | B2 | 2/2010 | Clayton |
| 7,921,847 | B2 | 4/2011 | Totz |
| 2001/0013345 | A1 | 8/2001 | Bertram |
| 2001/0054425 | A1 | 12/2001 | Bertram |
| 2005/0235998 | A1 | 10/2005 | Tresnak et al. |
| 2005/0279361 | A1 | 12/2005 | Chang |
| 2006/0081326 | A1 | 4/2006 | Zelin et al. |
| 2006/0180156 | A1 | 8/2006 | Baska |
| 2007/0021516 | A1 | 1/2007 | Hansel et al. |
| 2007/0074728 | A1 | 4/2007 | Rea |
| 2007/0102001 | A1 | 5/2007 | Brain |
| 2007/0119460 | A1 * | 5/2007 | Brain .................... 128/207.16 |
| 2007/0137651 | A1 | 6/2007 | Glassenberg et al. |
| 2008/0021273 | A1 | 1/2008 | MacKin |
| 2008/0029100 | A1 | 2/2008 | Glassenberg et al. |
| 2008/0115783 | A1 | 5/2008 | Brain |
| 2009/0044799 | A1 | 2/2009 | Qiu |
| 2009/0101140 | A1 | 4/2009 | Miller et al. |
| 2010/0059061 | A1 | 3/2010 | Brain |
| 2010/0089393 | A1 | 4/2010 | Brain |

* cited by examiner

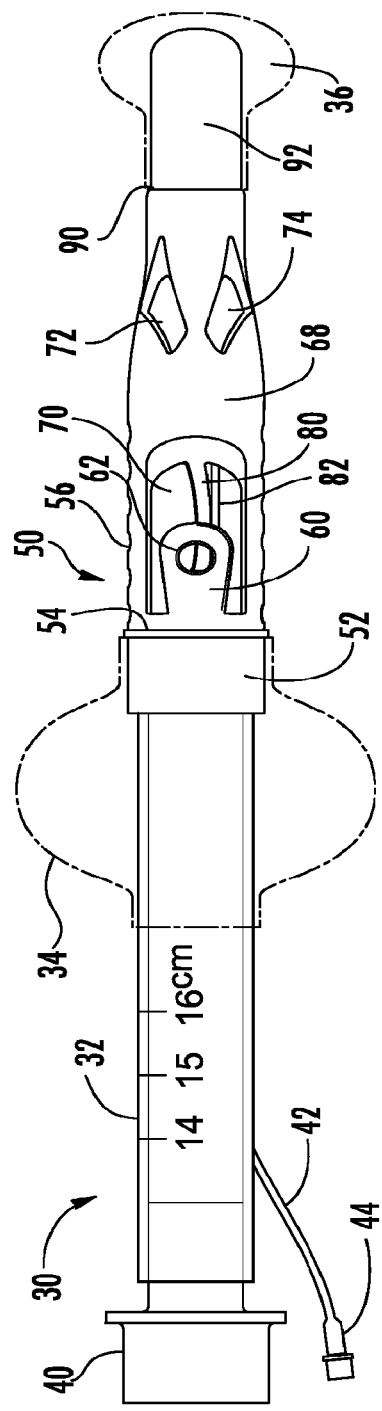
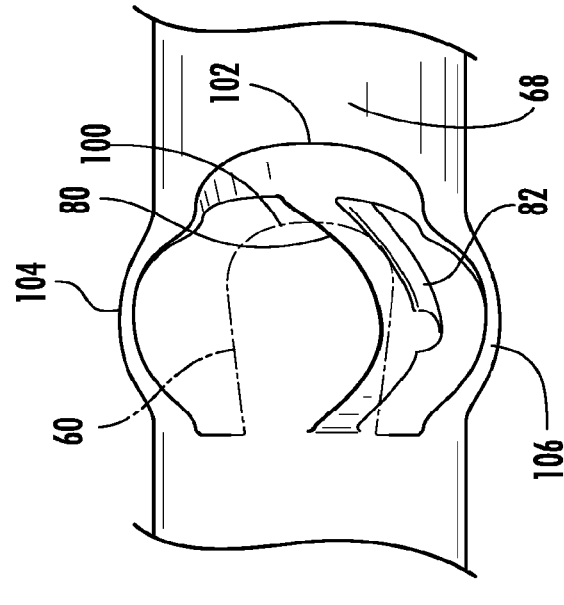
FIG. 1
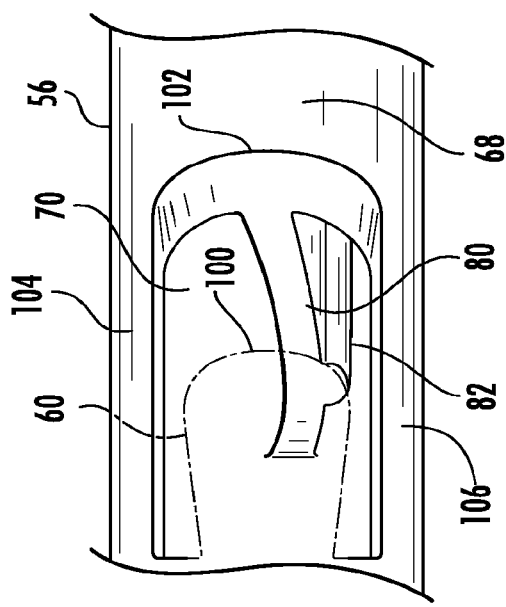
FIG. 2
FIG. 3

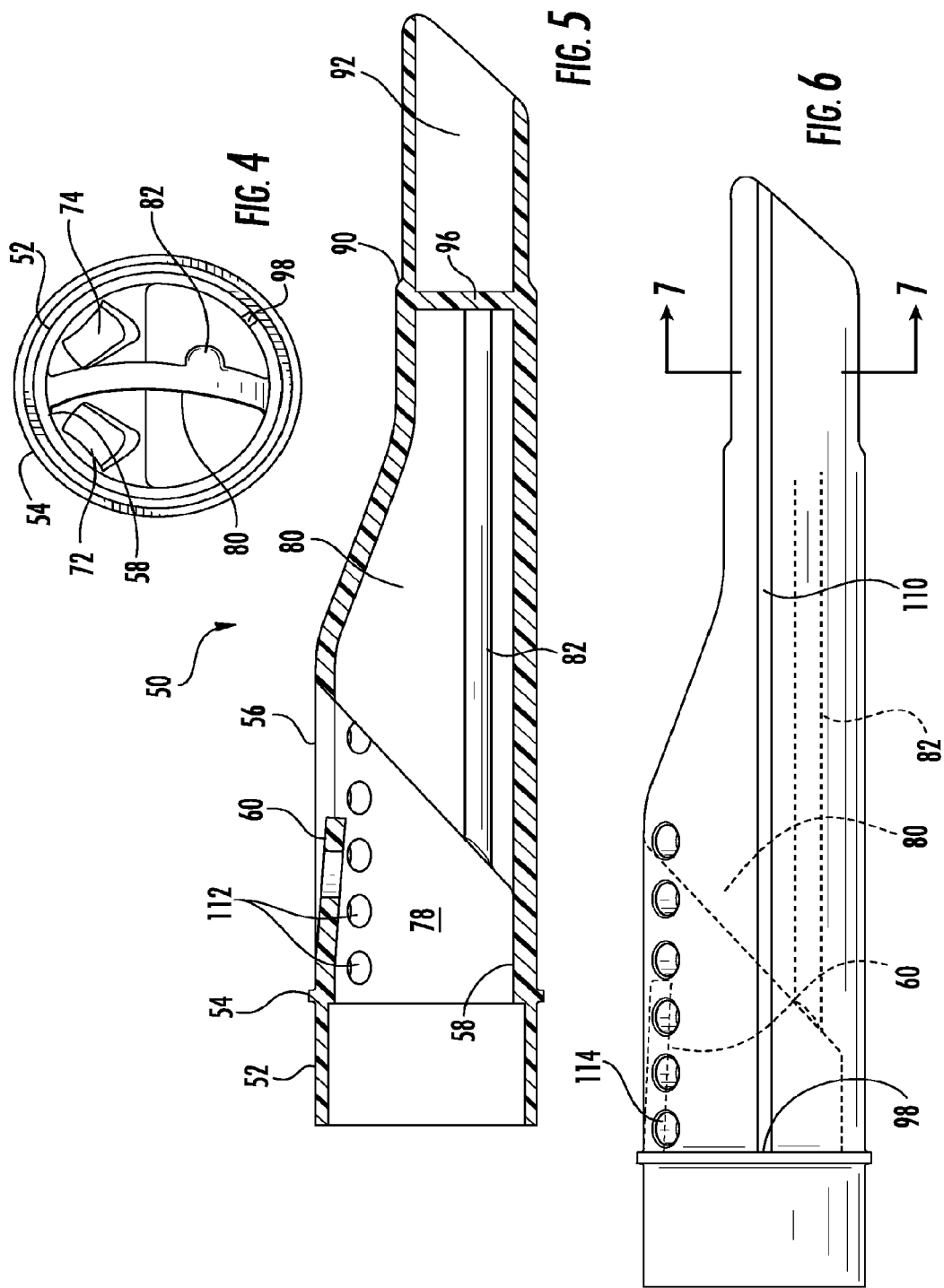

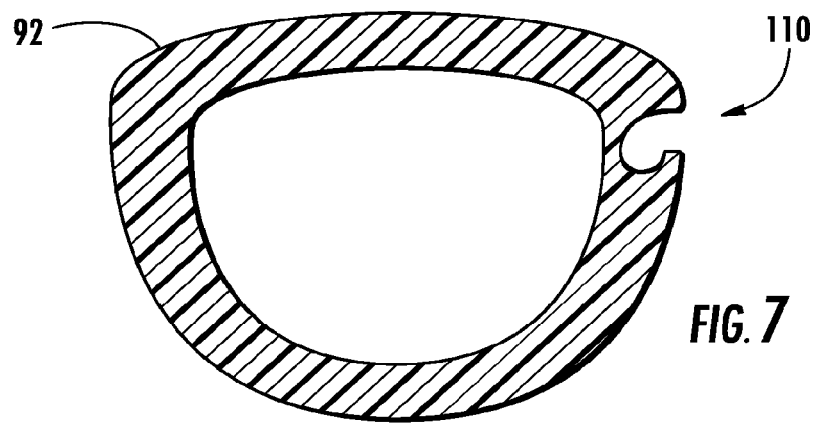
FIG. 7
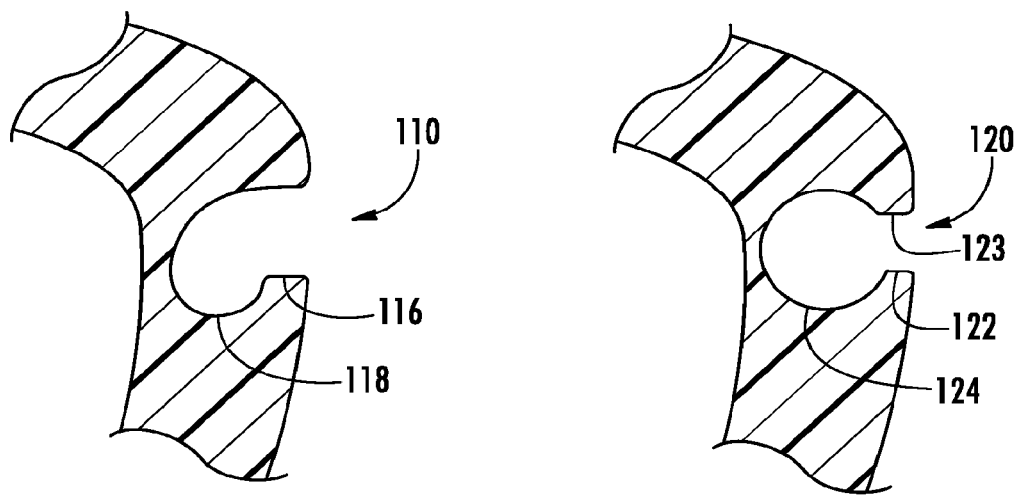
FIG. 8
FIG. 9
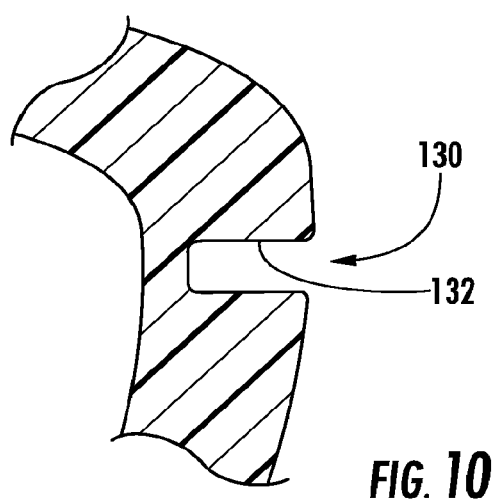
FIG. 10

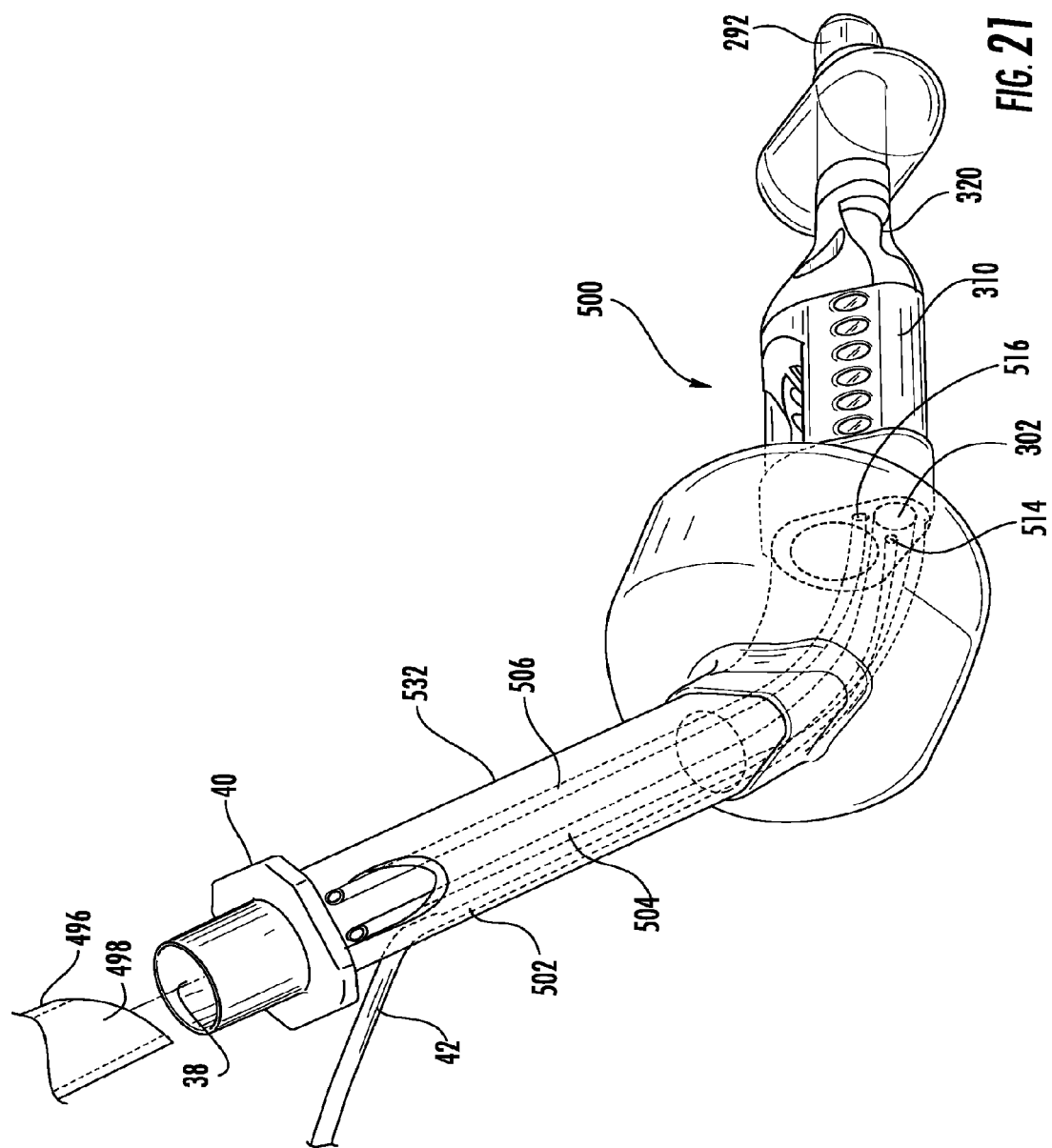

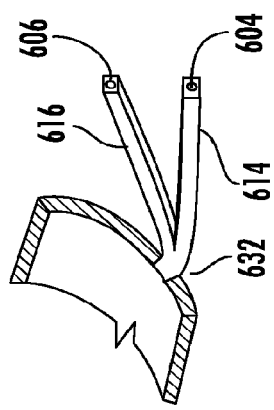
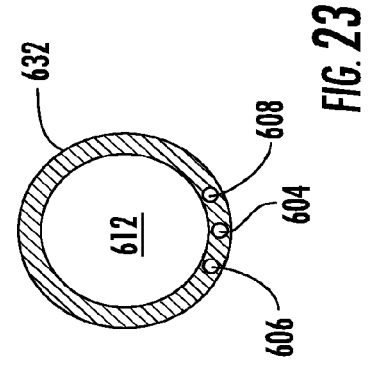
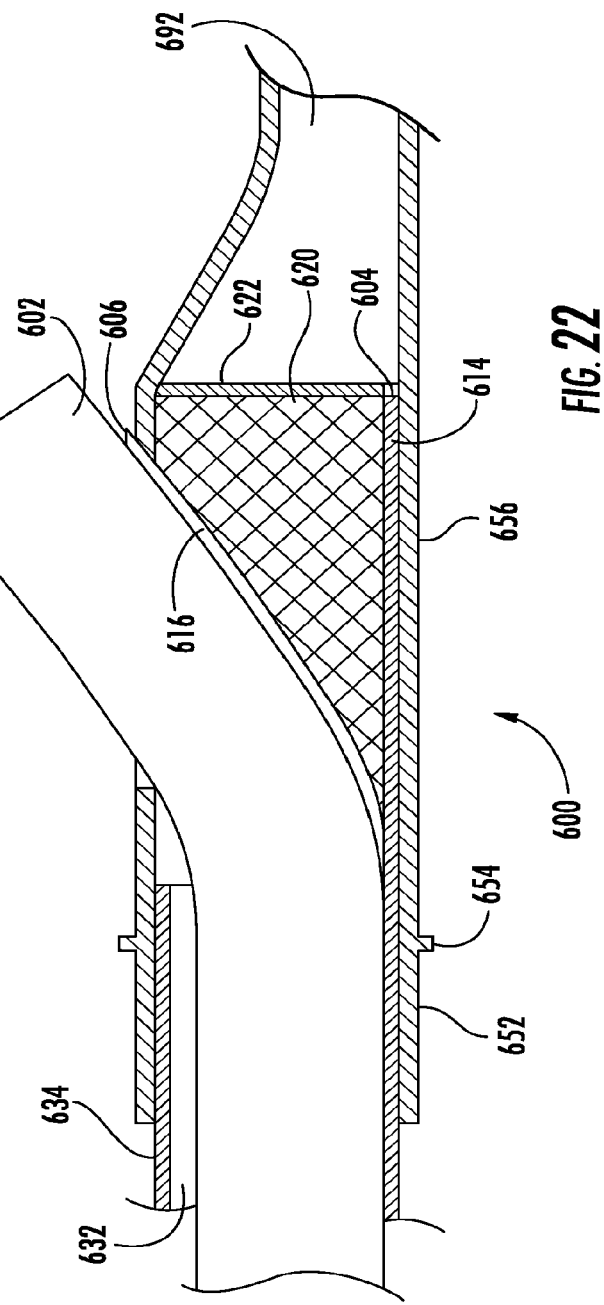

LARYNGEAL TUBE

CROSS-REFERENCE TO RELATED APPLICATIONS

This application is a U.S. national phase patent application of International Patent Application No. PCT/US11/26392, filed on 26 Feb. 2011, which claims the benefit of priority from U.S. Patent Application Ser. No. 61/308,898 entitled LARYNGEAL TUBE, filed on Feb. 27, 2010, the disclosures of both applications being expressly incorporated herein in their entirety by reference thereto.

STATEMENT REGARDING FEDERALLY SPONSORED RESEARCH OR DEVELOPMENT

This invention was made with government support under Award W81XWH-06-1-0019 awarded by the U.S. Army. The government has certain rights in the invention.

FIELD OF THE DISCLOSURE

The present disclosure relates generally to a medical instrument at least partially insertable into a patient to facilitate breathing and, more particularly, to a laryngeal tube.

BACKGROUND OF THE DISCLOSURE

Laryngeal tubes are designed to secure a patient airway during anaesthesia and cardiopulmonary resuscitation. A laryngeal tube may include a primary inflatable cuff, mask, or elastomeric cuff disposed on its distal end for blocking the oesophagus and a secondary inflatable or elastomeric barrier intermediate the distal and proximal ends for blocking the pharynx. Fluid communication is thereby established from the patient's mouth to the larynx. Due to space limitations in the buccal cavity, laryngeal tube improvements are desirable which provide functionality additional to securement of a patient airway.

SUMMARY OF THE DISCLOSURE

Embodiments of a laryngeal tube according to the disclosure, and methods for treating a patient with the laryngeal tube, are provided herein. In one embodiment, a laryngeal tube comprises a tubular member having a first lumen for receiving gases and delivering the gases to a patient; a nozzle having a body portion attached to the tubular member and a tip portion extending from the body portion, the body portion including a central cavity and an anterior opening which is in fluid communication with the central cavity, the anterior opening being adapted to receive therethrough a medical component inserted through the first lumen and the central cavity; a fluid barrier supported by the tip portion to block the oesophagus of the patient; a proximal service port supported by the tubular member; a service lumen fluidly coupled to the proximal service port; and a distal service port fluidly coupled to the service lumen and located near the anterior opening, the proximal service port, the service lumen and the distal service port defining a service passageway configured to perform a function associated with the larynx of the patient.

In another embodiment, a laryngeal tube comprises a tubular member having a first lumen for receiving gases and delivering the gases to a patient; a nozzle having a body portion attached to the tubular member and a tip portion extending from the body portion, the body portion including a central cavity and an anterior opening which is in fluid communication with the central cavity, the anterior opening being adapted to receive therethrough a medical component inserted through the first lumen and the central cavity; and a fluid barrier supported by the tip portion to block the oesophagus of the patient; wherein the body portion includes a tongue extending at least partially over the central cavity.

In a further embodiment, in a laryngeal tube as in any of the preceding embodiments, the nozzle further includes a guide component located in the central cavity, the guide component including an angled surface guiding the medical component through the central cavity toward the anterior opening. In one example, the guide component comprises a medial wall having a biasing feature causing the medial wall to bulge toward a biased side of the medial wall when the nozzle is dorsoflexed.

In a yet further embodiment, a laryngeal tube comprises a tubular member having a first lumen for receiving gases and delivering the gases to a patient; a nozzle having a body portion attached to the tubular member and a tip portion extending from the body portion, the body portion including a central cavity and an anterior opening which is in fluid communication with the central cavity, the anterior opening being adapted to receive therethrough a medical component inserted through the first lumen and the central cavity; and a fluid barrier supported by the tip portion to block the oesophagus of the patient, wherein the body portion further includes a guide component having an angled surface guiding the medical component through the central cavity toward the anterior opening.

In one example, the guide component comprises a medial wall having a biasing feature causing the medial wall to bulge toward a biased side of the medial wall when the nozzle is dorsoflexed. In one variation thereof, the biasing feature comprises at least one of a protrusion, a ridge, and a second material. In another variation thereof, the biasing feature comprises at least one of a cavity, an indentation, and a channel in the medial wall. In a further variation thereof, the biasing feature comprises at least a curvature of the medial wall.

In another example, the nozzle comprises a ventilation passageway on at least one side of the medial wall.

In a further example, the guide component comprises an insert. In a variation thereof, the insert is porous to enhance ventilation.

In another example, the nozzle further includes a tongue extending at least partially over the central cavity to block entry of the epiglottis into the central cavity and deflecting anteriorly to allow passage of the medical component through the anterior opening. In one variation thereof, the tongue has a tongue length and the anterior opening has an anterior opening length which is at least 25% longer than the tongue length. In another variation thereof, when the nozzle is dorsoflexed during normal use at least 10 degrees the tongue distal edge moves toward, without reaching or extending over, the anterior opening distal edge. In a further variation thereof, when the nozzle is dorsoflexed during normal use at least 45 degrees the tongue distal edge moves toward, without reaching or extending over, the anterior opening distal edge.

In a yet further embodiment, in a laryngeal tube as in any of the preceding embodiments, the medical component comprises at least one of an endotracheal tube and a stylet.

In another embodiment, a laryngeal tube as in any of the preceding embodiments further includes a proximal service port supported by the tubular member; a service lumen fluidly coupled to the proximal service port; and a distal service port fluidly coupled to the service lumen and located near the anterior opening, the proximal service port, the service lumen and the distal service port defining a service passageway configured to perform a function associated with the larynx of the patient.

In one example, the function comprises at least one of delivering a medication, sampling a fluid, and introducing a medical device.

In another example, the function comprises testing carbon dioxide levels in the larynx.

In a further embodiment, a laryngeal tube as in any of the preceding embodiments further includes a proximal inflation port supported by the tubular member; an inflation lumen fluidly coupled to the proximal inflation port; and a distal inflation port fluidly coupled to the inflation lumen and the fluid barrier to inflate the fluid barrier.

In one example, the inflation lumen is located within a wall of the tubular member and the laryngeal tube further includes an inflation bridge supported by the nozzle and fluidly coupling the inflation lumen with the distal inflation port. In one variation thereof, wherein the inflation bridge is a tube, the laryngeal tube further includes a channel in the nozzle supporting the inflation bridge.

The features of this invention, and the manner of attaining them, will become more apparent and the invention itself will be better understood by reference to the following description of the disclosed embodiments taken in conjunction with the accompanying drawings.

BRIEF DESCRIPTION OF THE DRAWINGS

FIG. 1 is an elevation view of a laryngeal tube according to an embodiment of the disclosure.

FIG. 2 is a partial view of the laryngeal tube of FIG. 1 in an unstrained condition.

FIG. 3 is a partial view of the laryngeal tube of FIG. 1 in a strained condition.

FIG. 4 is a cross-sectional plan view of the laryngeal tube of FIG. 1.

FIG. 5 is cross-sectional plan view of a portion of the laryngeal tube of FIG. 1.

FIG. 6 is plan view of a portion of the laryngeal tube of FIG. 1.

FIGS. 7 to 10 are partial sectional views illustrating additional features of the laryngeal tube of FIG. 1.

FIGS. 20 and 21 are perspective views of yet another embodiment of a laryngeal tube according to the disclosure.

FIGS. 22 to 24 are cross-sectional plan and perspective views of a further embodiment of a laryngeal tube according to the disclosure.

Figure 11:
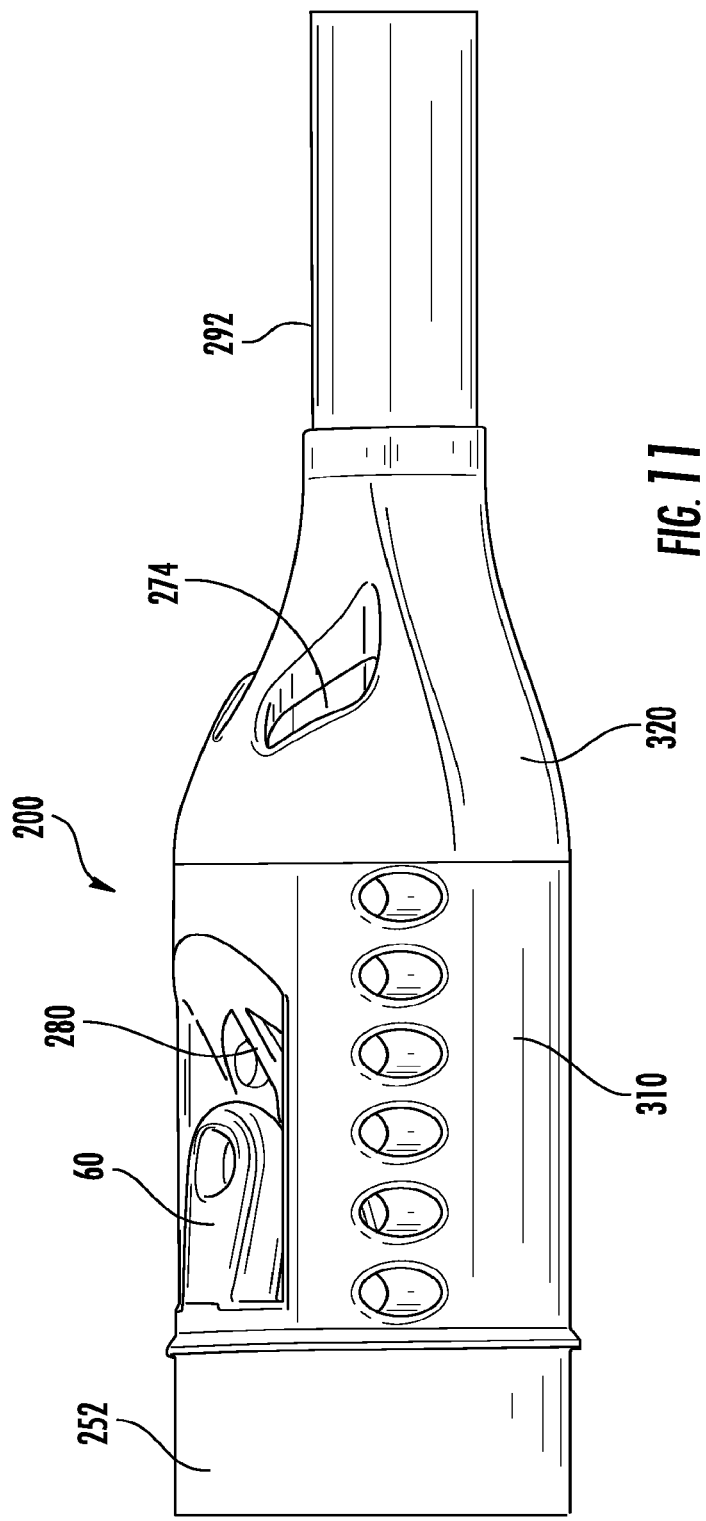
FIGS. 11 to 17 are plan, elevation and perspective views of a further embodiment of a laryngeal tube according to the disclosure.

Corresponding reference characters indicate corresponding parts throughout the several views. Although the drawings represent embodiments of the present disclosure, the drawings are not necessarily to scale and certain features may be exaggerated to better illustrate and explain the embodiments. The exemplifications set out herein illustrate embodiments of the disclosure in several forms and such exemplification is not to be construed as limiting the scope of the invention in any manner.

DETAILED DESCRIPTION

The embodiments discussed below are not intended to be exhaustive or limit the invention to the precise forms disclosed in the following detailed description. Rather, the embodiments are chosen and described so that others skilled in the art may utilize their teachings.

Embodiments of a laryngeal tube comprising features which secure a patient airway and provide additional functionality are disclosed herein. The features may be implemented independently of each other or together with other features. In one embodiment, a laryngeal tube according to the disclosure is provided comprising a tubular member and a nozzle. The distal end of the tubular member is coupled to the proximal end of the nozzle. The nozzle supports a distal fluid barrier. The laryngeal tube may also support a pharyngeal barrier. A barrier may comprise a cuff, inflatable or polymeric, a mask or any other device configured to engage tissue of the patient to prevent passage of fluid across or around the barrier. The distal fluid barrier blocks the oesophagus and the pharyngeal barrier blocks the naso and oropharynx. The tubular member includes a ventilation, or primary, lumen adapted to ventilate the space between the fluid barriers and also the larynx. The body of the nozzle comprises a posterior wall connected to lateral walls, an anterior opening disposed opposite the posterior wall, and a central cavity therebetween. Gases introduced through the proximal end of the ventilation lumen may enter the larynx through a plurality of holes disposed on the nozzle walls. Medical components, or devices, may be introduced into the larynx through the ventilation lumen. Exemplary medical components include an endotracheal tube, stylet, boogie, endoscope, laryngoscope and other medical components suitable to treat the patient. An exemplary embodiment of a laryngeal tube showing a tubular component, a distal fluid barrier, a pharyngeal barrier, a nozzle with a body portion having a central cavity and an anterior opening, and a distal nozzle portion is illustrated in FIG. 21. Additional features such as a service passageway, an inflation lumen and a suction passageway comprising a suction lumen are also described therein. The laryngeal tube illustrated in FIG. 21 may include any of the features described below.

When one of the fluid barriers is inflatable, the tubular member may comprise an inflation lumen within a wall of the tubular member. The inflation lumen is coupled at its proximal end to an inflation tube which may comprise a check valve. A pump coupled to the inflation tube inflates the inflatable fluid barrier and the check valve deflates the fluid barrier. The distal end of the inflation lumen may be coupled to an inflation bridge disposed within a channel provided in the nozzle. Alternatively, the nozzle may comprise an inflation lumen configured to connect with the tubular member inflation lumen to thereby establish fluid communication between the inflation tube and the nozzle. The distal end of the inflation bridge may be in fluid communication with the distal fluid barrier. When fluid is provided by the pump, portions of the fluid move through the tubular member inflation lumen to the inflation bridge and from there to the inflatable cuff. A notch or valve provided in any one of the inflation lumens or the inflation bridge may establish fluid communication to inflate an inflatable pharyngeal barrier.

In another embodiment of a laryngeal tube according to the disclosure, a tongue is provided to block entry of the epiglottis into the central cavity while permitting the medical component to pass through the anterior opening. The laryngeal tube includes at least the tubular component, the nozzle, the central cavity and the anterior opening described above. The tongue may extend from the proximal edge of the anterior opening or proximal end of the central cavity over a portion of the central cavity. The tongue may also extend from a lateral wall. The tongue may be angled inwardly so as to prevent its distal end from engaging tissue of the patient. Advantageously, the length of the tongue may be defined to prevent the medical component from exiting the nozzle through the proximal end of the anterior opening while being short enough that the distal end of the tongue does not reach the distal edge of the anterior opening when the laryngeal tube is strained. As described further below with reference to a guiding component with a biasing feature, the tongue may advantageously extend from the side of the nozzle opposite the biased side so that the free edge of the tongue covers the side of the central cavity through which the medical component will exit due to the guidance provided by the biasing feature.

In one variation of the present embodiment, when the nozzle is dorsoflexed, the lateral walls deflect outwardly and the tongue distal edge moves toward the anterior opening distal edge without contacting or extending over the anterior opening distal edge. A strained condition is evident when the nozzle is dorsoflexed at least 1 degree. The nozzle may be dorsoflexed 10 degrees, 45 degrees, and even more during normal use. In one example, the distance between the distal end of the tongue and the distal edge of the anterior opening, which may be referred to as the gap length, ranges between 1 and 25 millimeters in the unstrained condition. In another example, the gap length ranges between 3 and 18 millimeters in the unstrained condition. In a further example, the gap length ranges between 5 and 12 millimeters in the unstrained condition. In a yet further example, the length of the anterior aperture is 25% greater than the length of the tongue (measured from the point of attachment to the body of the nozzle to the tongue distal edge). In another variation, when the nozzle is dorsoflexed during normal use at least 10 degrees the tongue distal edge moves toward, without reaching or extending over, the anterior opening distal edge. In a further variation, wherein when the nozzle is dorsoflexed during normal use at least 45 degrees the tongue distal edge moves toward, without reaching or extending over, the anterior opening distal edge. These advantages are achieved by configuring the length of the tongue according to design choices including a desired range of dorsoflexion.

In a further embodiment of a laryngeal tube according to the disclosure, a guide component is provided located in the central cavity and having an angled surface to guide the medical component through to the anterior opening. The laryngeal tube includes at least the tubular component, the nozzle, the central cavity and the anterior opening described above. The laryngeal tube may also include the tongue. In one form thereof, the guide component is an insertion piece as described below with reference to FIG. 22. In another form thereof, the guide component is a medial wall including the angled surface which may be longitudinally aligned. The proximal end of the angled surface is nearer the posterior wall and the distal end of the angled surface is nearer the anterior opening. Thus, the medial wall does not block the anterior opening. In one example, biasing features are provided on one or both sides of the medial wall to laterally bias the medial wall such that when the nozzle is dorsoflexed, the medial wall bulges in the biased direction, e.g. bulges toward one side of the medial wall. Exemplary biasing features include ridges, protrusions, channels, cavities, thickness gradients, combinations of materials, layers of materials, curvature, and any other feature suitable to bias the medial wall. Many endotracheal tubes have bevelled or slanted tips, where one lateral side extends further than the other. Often, the right side of the tube extends further than the left. The medial wall may be biased, in that case, to bulge toward the right side in the strained condition to enable the tube to exit the anterior opening without being constrained by any parts of the nozzle. The same effect is achieved with left-side bias for tubes in which the left side extends beyond the right side.

In yet another embodiment of a laryngeal tube according to the disclosure, a service passageway is provided to perform a service function associated with the larynx. The laryngeal tube includes at least the tubular component, the nozzle, the central cavity and the anterior opening described above. The laryngeal tubes may include a tongue, a guide component, suction features, and other disclosed features. In some variations, those features, or any one of them, are excluded. In the present embodiment, the passage way includes a service lumen fluidly coupled to a proximal service port supported by the tubular component. As described with reference to the inflation lumen, the service lumen may be provided in the wall of the tubular component or in a service tube attached to the tubular component, the fitting or the nozzle. Exemplary functions include delivering medication, sampling a fluid, introducing a medical device, testing carbon dioxide levels in the larynx, and any other suitable function operable through the service lumen. Gas samples may be extracted through the service passageway for testing. Sensors may be introduced into the larynx while the patient is intubated. Medications may be delivered when the test results or the sensed information reach predefined levels. Exemplary service passageways are disclosed with reference to FIGS. 20 to 24.

Exemplary embodiments according to the disclosure will now be described with reference to FIGS. 1 to 8. Referring to FIG. 1, an elevation view of a laryngeal tube 30 is provided. Laryngeal tube 30 comprises a tubular member 32 and a nozzle 50 having a body portion 56 and a tip portion 92. Tubular member 32 is connected at its proximal end to a fitting 40 which is adapted to connect a ventilation lumen within tubular member 32 to a source of gases such as a ventilator. Gases pass through tubular member 32 into nozzle 50 and exit through an anterior opening 70 and orifices 72, 74, 112 and 114 (orifices 112 and 114 are shown in FIGS. 5 and 6). For illustration purposes the side of laryngeal tube 30 in which orifices 112 are located will be referred to as the left side and the side in which orifices 114 are located as the right side. Consequently, body portion 56 includes a posterior wall 58, a left wall 104 and a right wall 106 defining a central cavity 78. Nozzle 50 further includes a tongue 60 showing an optional aperture, illustratively aperture 62, a medial wall 80, biasing features, and an anterior wall 68. Tongue 60 is provided at least to prevent the epiglottis from entering central cavity 78. In the present embodiment, biasing features include a ridge 82 provided on one side of medial wall 80 and the curvature of wall 80 (best seen in FIGS. 2 and 4). One or more apertures, having any shape, may be provided in tongue 60 to increase ventilation. Exemplary shapes include round, oval, square and elongate. The proximal end of nozzle 50 comprises a ridge 54 separating body portion 56 from a flange 52. The fluid barriers, illustratively inflatable cuffs 36 and 34, respectively, are also shown. An edge 90 is provided proximally of tip portion 92 to facilitate mounting of a distal fluid barrier onto tip portion 92. In a variation of the present embodiment, nozzle 50 does not include tongue 60. In another variation of the present embodiment, medial wall 80 does not include biasing features. In yet another variation of the present embodiment, medial wall 80 extends between the right and left walls of the nozzle.

Referring now to FIGS. 2 and 3, FIG. 2 shows a portion of nozzle 50 in an unstrained condition and FIG. 3 shows the same portion under strain to illustrate bulging or outward (lateral) extension of walls 104 and 106. FIG. 2 illustrates a distal edge 100 of tongue 60 partially covering anterior opening 70 and being separated from a distal edge 102 of anterior opening 70. Medial wall 80 is shown with right-side bias based at least on its curvature. Medial wall 80 may be located anywhere within central cavity 78 and does not necessarily have to be located equidistantly between walls 104 and 106. FIG. 3 also illustrates distal advancement of edge 80 relative to the unstrained nozzle and a reduced gap distance between edge 100 and edge 102. Advantageously, when the bevelled portion of an endotracheal tube enters central cavity 78 it encounters medial wall 80 which guides the bevelled portion of the tube through anterior opening 70, even in the strained condition.

FIG. 5 illustrates another embodiment of the disclosure showing tongue 60 inclined toward posterior wall 58 to prevent engagement of tongue 60 with the patient's tissue. In the embodiment shown, a wall 96 separates tip portion 92 from body portion 56. In further embodiments, wall 96 exhibits an opening to establish fluid communication with the esophagus. A suction tube may pass through the opening. Alternatively, a suction tube or suction channel may sealingly couple an opening in wall 96 (as shown in FIG. 22).

Referring now to FIGS. 4 and 6, FIG. 4 is a plan view of the proximal end of nozzle 50 showing an aperture 98 (also shown in FIG. 6) provided to couple an inflation lumen disposed in a wall of tubular member 32 to an inflation bridge (not shown) supported by a channel 110. The inflation bridge reaches tip portion 92 to inflate inflatable cuff 36. Alternatively, inflation tube 42, optionally including a check valve 44 (shown in FIG. 1), may extend to the distal end of tubular member 32 and fluidly couple through aperture 98 with the inflation bridge. Check valve 44 allows gases to flow toward nozzle 50 and prevents the gas from flowing back thereby maintaining the inflatable cuffs inflated. Check valve 44 may be configured to permit flow-back if inflation pressure exceeds a predetermined level. In one variation, check valve 44 comprises a biased detent wherein the biasing force is calibrated to the predetermined level. In one form thereof, a pressure indicator is provided in inflation tube 42 to indicate the pressure level or produce an alarm if the pressure is too high or too low, e.g., emit a particular sound, change color etc. In another form thereof, pressure gages display colors corresponding to pressure ranges, e.g., normal, low, and high.

FIGS. 7 to 10 illustrate exemplary channel profiles to support the inflation bridge. Channels 110, 120 and 130 are shown. The profile of channel 110 has a circular portion 118 and a wall portion 116. In use, the inflation bridge is pressed against the opening of the channel until it slips into the circular portion of the channel. Advantageously, channel 110 permits insertion of the inflation bridge and snug receipt thereof without requiring substantial force to press the inflation bridge into channel 110. Of course, material choices will impact the rigidity and flexibility of channel 110 and thus affect the amount of required force. Channel 120 comprises walls 122 and 123 and a round slot 124. The provision of two walls requires more insertion force as compared to channel 110 if the inflation bridge is to be snugly retained in the round slot. On the other hand, channel 130 exhibits no walls and requires the least amount of insertion force. The width of channel 130 may be configured to be slightly narrower than the diameter of the inflation bridge to retain the inflation bridge in place by compression. Alternatively, the inflation bridge may be bonded inside any one of channels 110, 120 or 130.

FIGS. 11 to 19 disclose embodiments of a laryngeal tube according to the disclosure with features configured to suction fluids. The laryngeal tube includes at least the tubular component, the nozzle, the central cavity and the anterior opening described above. Generally, embodiments of a laryngeal tube with suction features are similar to embodiments of laryngeal tubes disclosed in FIGS. 1 to 10 and as such may include a tongue, a guide component, biasing features, and other disclosed features. In some variations, those features, or any one of them, are excluded. In the present embodiments a suction tube is provided and fluidly coupled to a lumen provided in the nozzle to form a suction lumen that enables a practitioner to connect a pump to the tube to suction fluids from the patient. The tube may be attached to the tubular member of the laryngeal tube at its proximal end and connected to a suction lumen provided in the wall of the tubular member in the manner disclosed with reference to FIG. 1. The tube may also be attached to the tubular member and subsequently be fluidly coupled to the nozzle. An exemplary nozzle 200 is disclosed with reference to FIGS. 11 to 17. An exemplary nozzle 400 is disclosed with reference to FIGS. 18 and 19.

Figure 14:
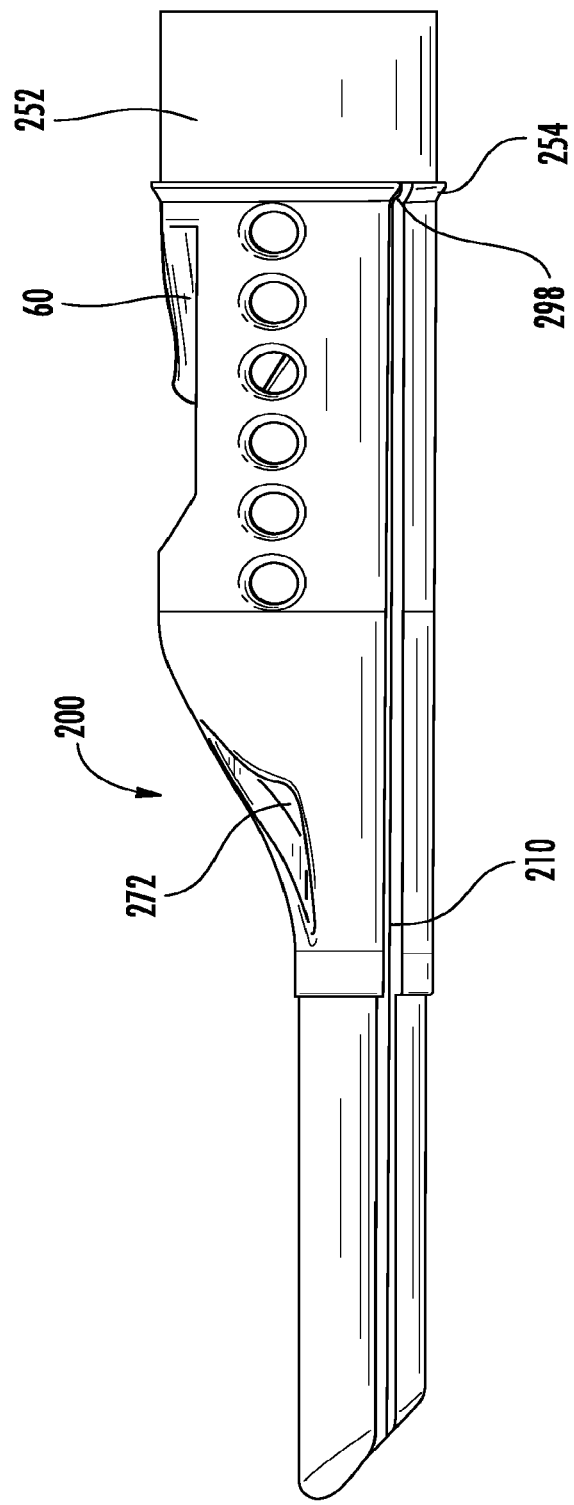
Figure 15:
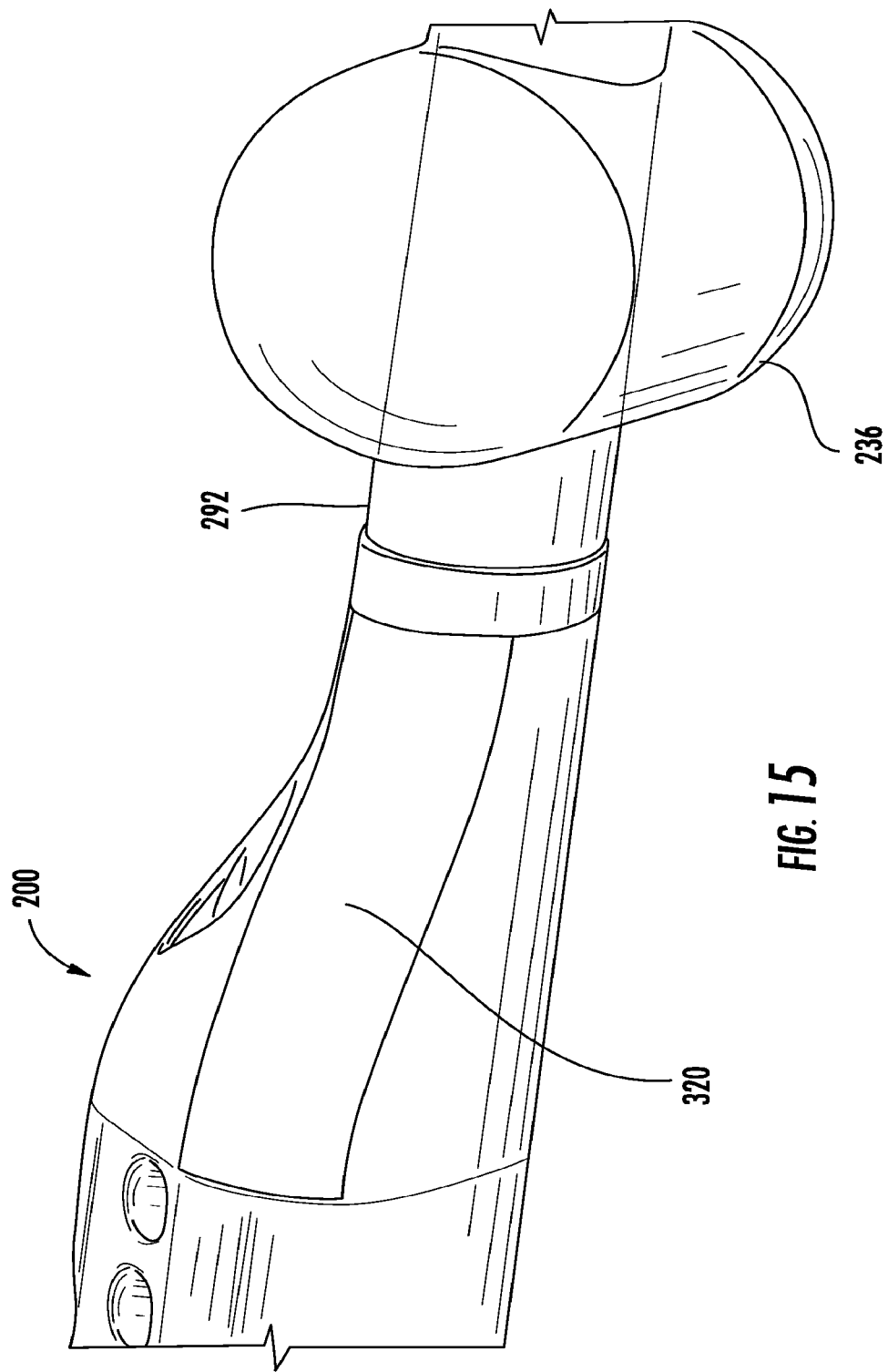
Figure 16:
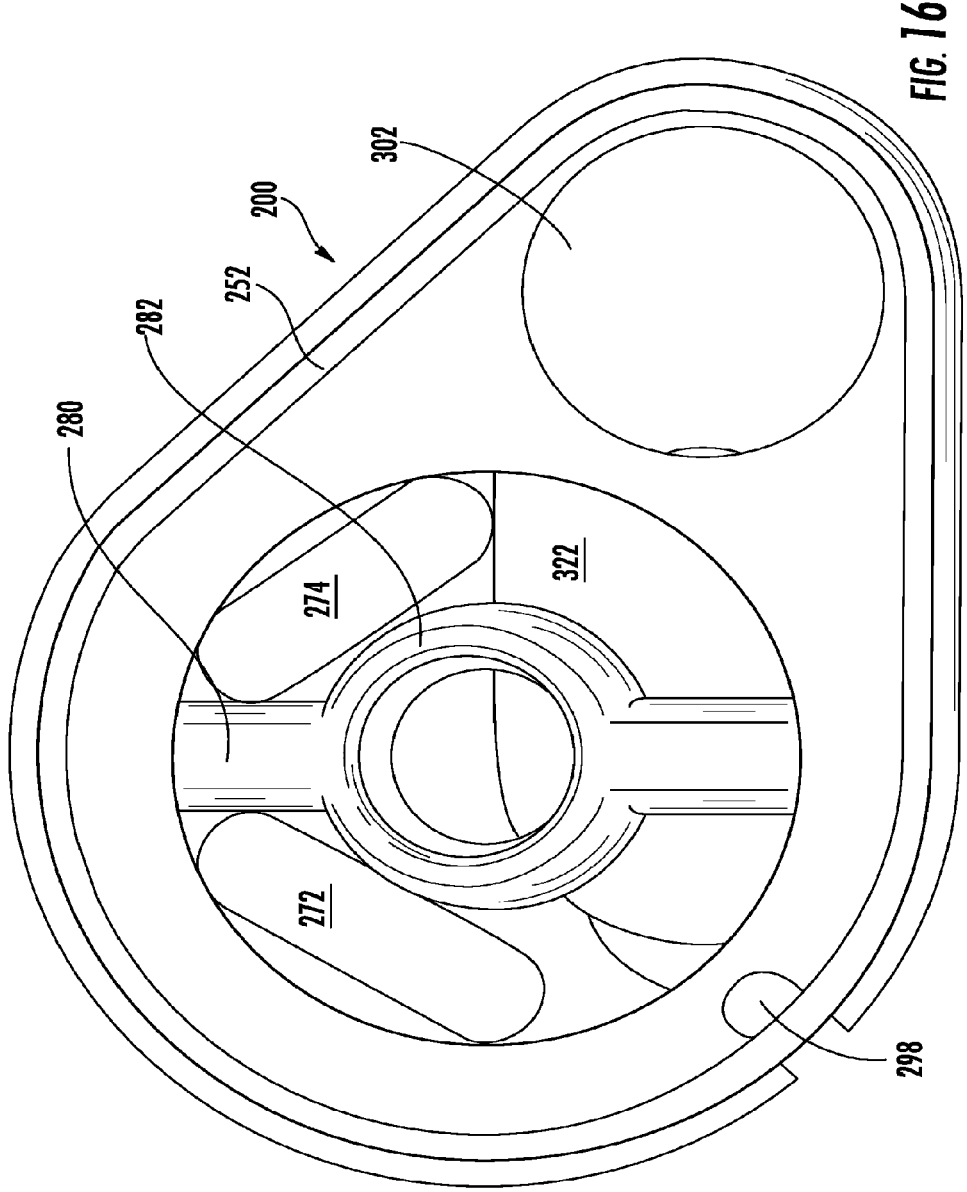

Referring to FIGS. 11 to 17, nozzle 200 has a medial wall 280 and an external wall 310 of a suction lumen 302 (shown in FIG. 16). In use, lumen 302 will be in fluid communication with a tip portion 292 and will discharge fluids through an aperture 294 (shown in FIG. 17). A suction tube may pass through lumen 302 and into tip portion 292 to establish fluid communication with the esophagus. The tube may be supported by an open channel 320. In another form thereof, a channel cover (not shown) is provided to sealingly close open channel 320 establishing fluid communication between lumen 302 and tip portion 292 without a tube. A tube may also be provided passing through channel 320 after it is closed with a cover to extend the suction lumen. A flange 252 performs a similar function as flange 52. Further, flange 252 is configured to receive a suction tube or a fitting (not shown) which is coupled to a suction tube. The suction tube may pass through, or may be sealingly coupled to, lumen 302 to enable suction of fluids therethrough.

Figure 12:
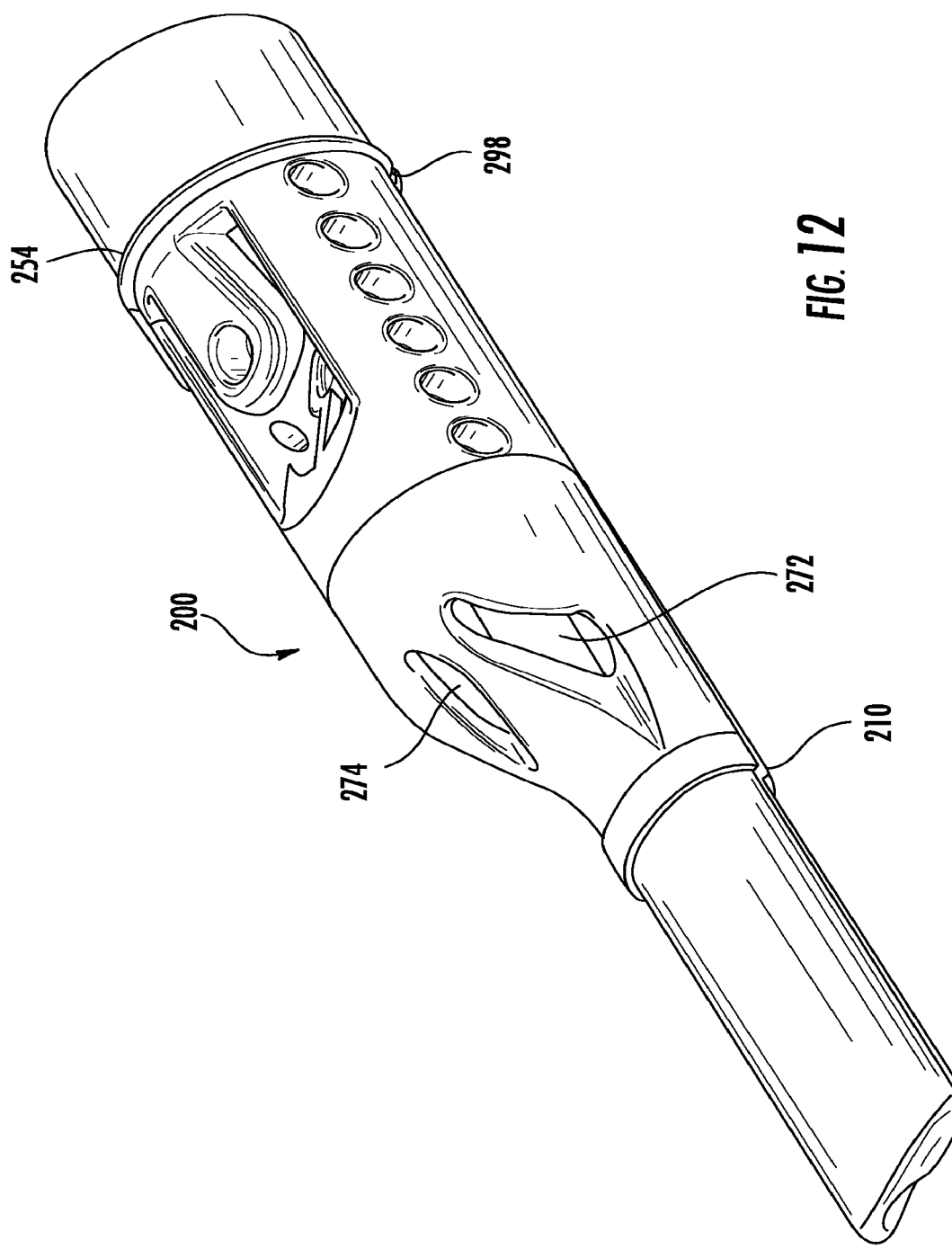
Figure 13:
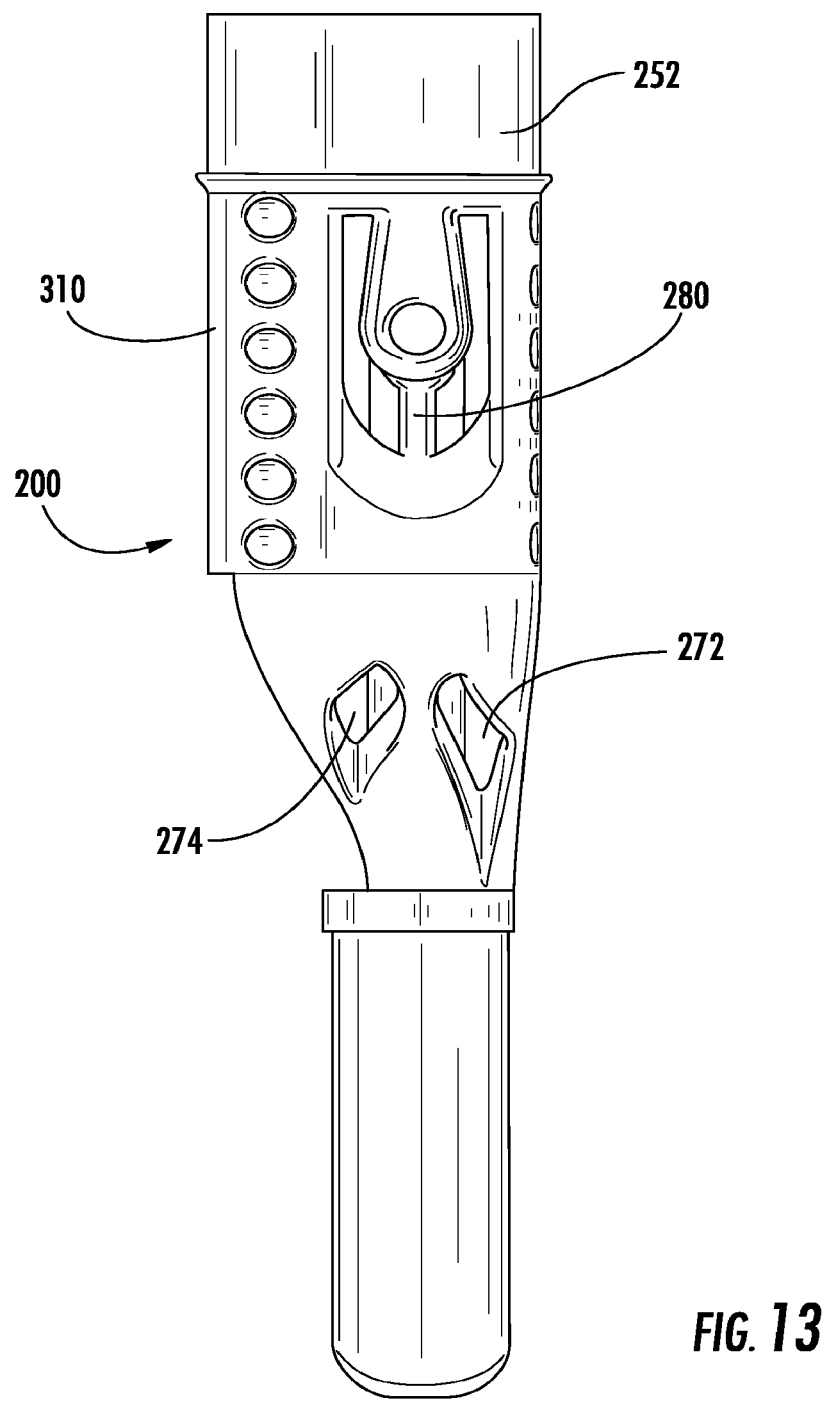

FIGS. 12 and 13 show differences between orifices 272 and 274 resulting from the reservation of space below orifice 274 for the provision of an open channel, lumen, and/or a suction tube. FIGS. 12 and 14 illustrate a channel 210 provided to support an inflation bridge and a aperture 298 proximal to a ridge 254 for coupling the inflation bridge to a lumen in the tubular member of the laryngeal tube. FIG. 15 illustrates a distal fluid barrier 236 supported by tip portion 292 which extends through distal fluid barrier 236 to enable suctioning of fluids. An elongate aperture inside tip portion 292 (not shown) is provided for that purpose.

Figure 17:
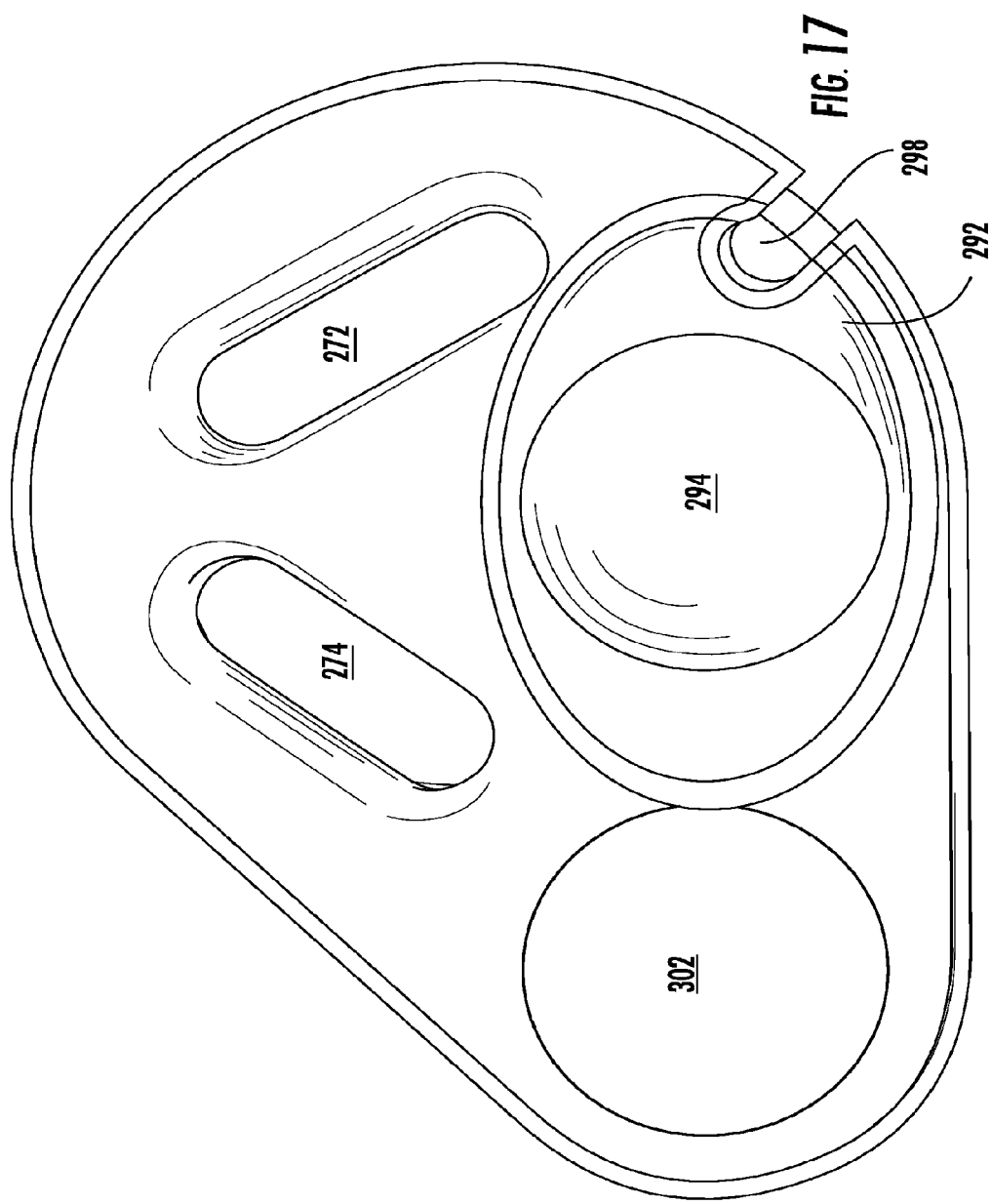

FIG. 16 is a plan view of the proximal end of nozzle 200. The tubular member may be integrally formed with the suction tube, and the two portions together may then be sealingly coupled to flange 252. Alternatively, a fitting attached to the tubular member and the suction tube may be received by flange 252. The external surface of the fitting and the internal surface of flange 252 form a seal. The tubular member establishes fluid communication with central cavity 78 while the suction tube establishes fluid communication with lumen 302. A surface 322 is the internal surface of open channel 320. A medial wall 280 comprises a device guide feature, illustratively a ring portion 282, which is provided to facilitate smooth insertion of tubes and devices of various diameters through central cavity 78 and anterior opening 70 even without biasing medial wall 280. Endotracheal tubes having diameters smaller than 8.0 mm, for example 7.0 mm, may be introduced. Ring portion 282 causes the tubes to bend toward anterior opening 70 and to smoothly pass therethrough. FIG. 17 is a plan view of the distal end of nozzle 200.

Figure 18:
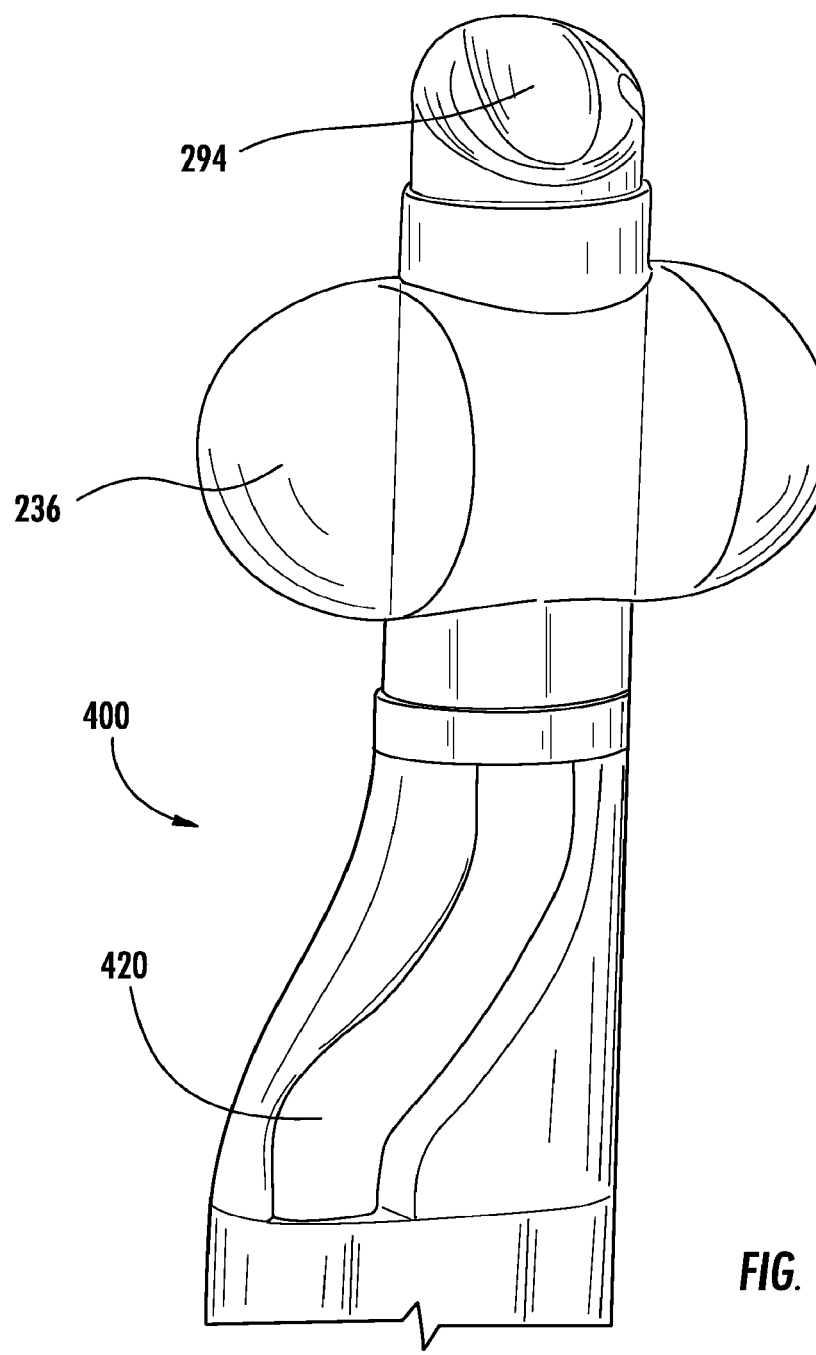
FIGS. 18 and 19 are perspective and elevation views of a yet further embodiment of a laryngeal tube according to the disclosure.
Figure 19:
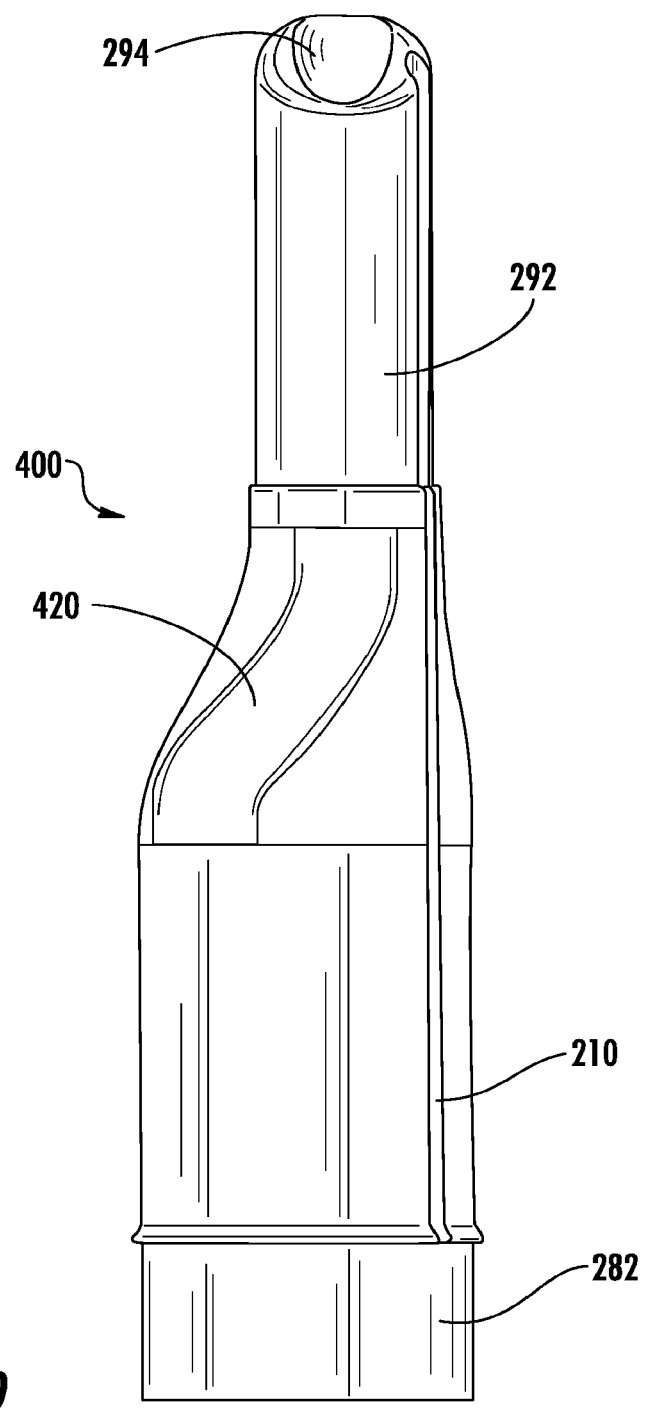

Referring to FIGS. 18 and 19, nozzle 400 is shown therein illustrating a different position of suction features compared to nozzle 200. An open channel 420 is shown on the posterior side of nozzle 400. Open channel 420 functions similarly as open channel 320.

Figure 20:
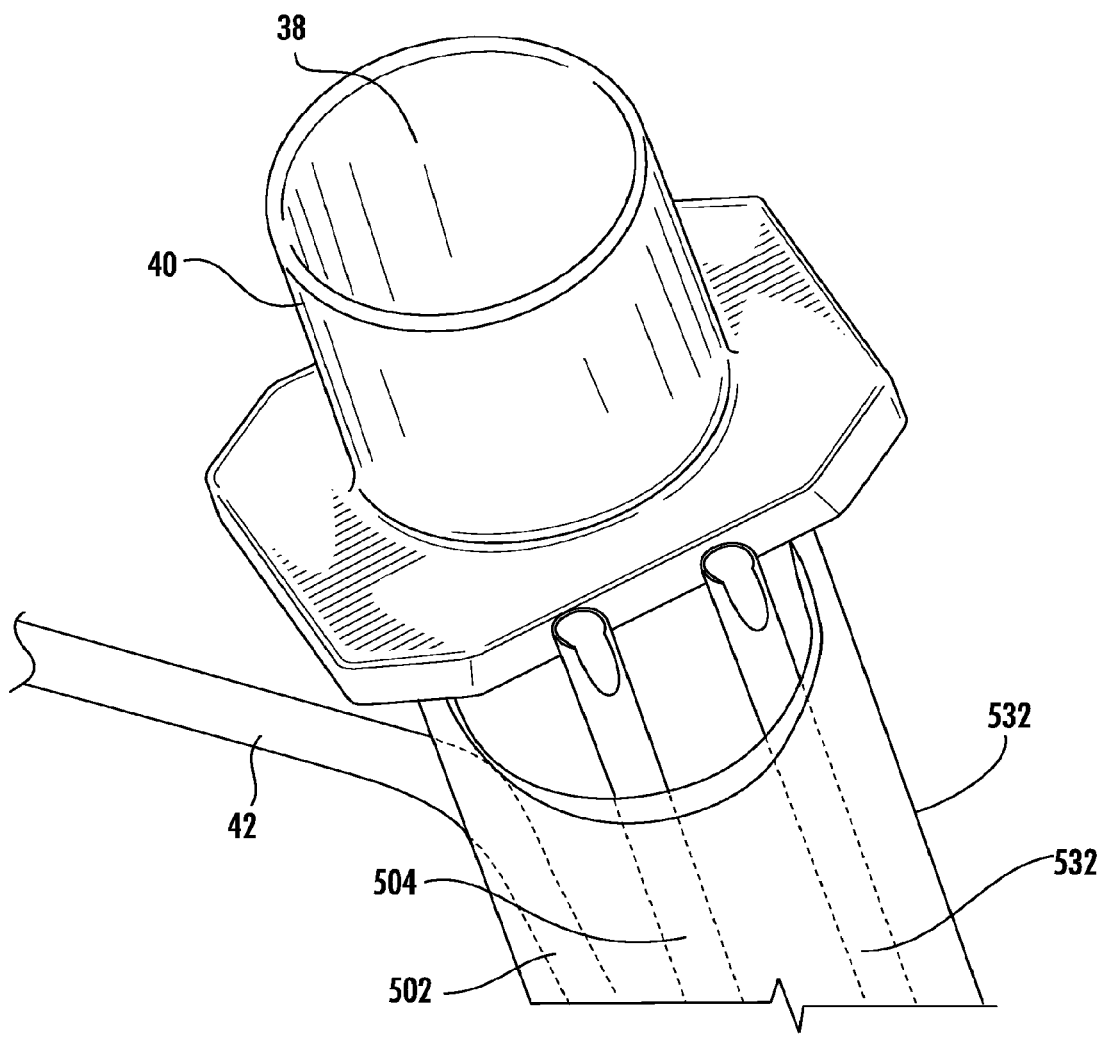

FIGS. 20 to 24 disclose embodiments of a laryngeal tube according to the disclosure with features configured to perform a function associated with the larynx of the patient. Generally, embodiments of a laryngeal tube with functional features associated with the larynx are similar to embodiments of laryngeal tubes disclosed in FIGS. 1 to 19 and as such may include a tongue, a guide component, suction features, and other disclosed features. In some variations, those features, or any one of them, are excluded. In the present embodiments a service lumen is provided to enable a practitioner to perform a function. An exemplary laryngeal tube illustrating a tubular member 532 and a nozzle 500 is shown in FIGS. 20 and 21. An exemplary laryngeal tube illustrating a tubular member 632 and a nozzle 600 is shown in FIGS. 22 to 24.

Referring to FIGS. 20 and 21, tubular member 532 comprises multiple lumens within a wall of the tubular member, illustratively inflation lumen 502, suction lumen 504 and service lumen 506. Inflation tube 42 is fluidly coupled with lumen 502. Suction lumen 504 is fluidly coupled with suction tube 302. Service lumen 506 is fluidly coupled to a lumen 516 provided in nozzle 500. Advantageously, nozzle 500 enables a patient to receive gases and medications, to sample gases, and to suction fluids, without substantially increasing the cross-sectional area of nozzle 500. Fitting 40 comprises an orifice 38 for receiving gases and inserting a tubular member (an exemplary tubular member 602 is shown in FIG. 22). An exemplary section of an endotracheal tube 496 having a ventilation lumen 498 to deliver gases to the patient is shown. Endotracheal tube 496 may be inserted through orifice 38 and guided through the anterior opening of nozzle 500 and the vocal cords of the patient. In one form thereof, service lumen 516 extends through the body of nozzle 500 to a distal port (not shown) positioned on the anterior surface of nozzle 500. In one example, service lumen 516 is formed in a wall of nozzle 500. In another example, a tube, similar to the inflation bridge, is attached within the central cavity of nozzle 500. A further example of a service lumen is disclosed below.

Referring now to FIGS. 22 to 24, nozzle 600 is shown therein comprising a body 656, a flange 652, a tip portion 692 and an insert piece 620. Also shown is a tubular member 632 having a wall 634 and wall portions 614 and 616. Generally, insert piece 620 comprises an insert which may also include a distal barrier surface and which may be attached to portions 616 of tubular member 632 before insertion into the body of a nozzle to form nozzle 600. Use of an insert piece provides a simplified method of constructing a nozzle with service function features. In one form thereof, insert piece 620 is gas permeable. Exemplary materials that provide gas permeability include open-celled foam, extruded honeycomb structures, elastomeric injection molded structures, or any other gas porous materials. In one example, porosity is greater than 10% to enable gases passing through a lumen of tubular member 632 to discharge through insert piece 620 and orifices on the wall surfaces of the body of nozzle 600. In another example, insert piece 620 exhibits porosity greater than 35%. In a further example, insert piece 620 exhibits porosity greater than 50%. A barrier wall 622 is provided to prevent gas discharge into the oesophagus. Barrier wall 622 may be attached or coated onto insert piece 620 or may be integrally formed with the body of nozzle 600. Tubular member 632 is inserted into flange 652. An endotracheal tube 602, having a lumen 612 within, is shown passing through the anterior opening of nozzle 600. A suction lumen 604 extends through wall 634 and portion 614 of wall 634, and a service lumen 606 extends through wall 634 and portion 616 of wall 634. A distal port of portion 616 is shown extending outside nozzle 600 near the anterior opening. Service lumen 606 may discharge medication into the larynx. Carbon dioxide measurements may be performed by sampling gases or introducing a carbon dioxide sensor through service lumen 606. Portions 614 and 616 are best shown in FIG. 24 as strips of wall 634 of tubular member 632.

Although porous materials tend to be flexible, additional flexibility may be provided to nozzle 600 by removing partial slices of portion 620 from its posterior side so that when stress is applied to the nozzle, insert piece 620 will easily dorsoflex. The partial slices may comprise cross-sectional portions of insert piece 620 which do not remove material from the anterior portion of insert piece 620. In another form thereof, a plurality of slits are provided as a means to remove portions of material from insert piece 620. Wall portion 616 may be widened to provide a sliding surface for tube 602. In one example, wall portion 616 is at least 5 mm wide. In another example, wall portion 616 is at least 8 mm wide. Nozzle 600 may be injection molded. To form portions 614 and 616, a portion of tubular member 632 may be cut so that portions 614 and 616 remain. Insert piece 620, with barrier wall 622 attached, may then be bonded to portions 614 and 616 before the assembly is inserted into nozzle 600.

While many features were described above, the invention is not limited to the exemplary embodiments. In another form thereof, ridges are provided on both sides of the medial wall to bias the medial wall. In a further form thereof, laminates or inserts adjacent to one side of the medial wall, without ridges or protrusions, bias the wall. In a yet further form thereof, apertures are provided through the medial wall. The profile of the apertures provides the bias. Exemplary profiles include conical, cylindrical, rectangular, and any other suitable profile. The function of directing a tube towards the anterior opening may also be performed by an insert connecting the posterior wall of the body of the nozzle with the distal edge of the anterior opening. The insert may be permanently attached, for example adhesively bonded, to the nozzle, or pressure-fit. Different inserts may be provided configured to operate with different devices. Larger inserts may be provided to function with smaller tubes and smaller inserts may be provided to function with larger tubes.

In one variation thereof, the insertion portion includes an angled surface guiding the passage of a medical component through the central cavity and anterior opening of nozzle 600. As shown in FIG. 22, portion 616 rests against the angled surface. Endotracheal tube 602 may slide on portion 616. In another example, portion 616 is embedded in a channel provided in the insertion piece and endotracheal tube 602 rides on the angled surface of the insertion piece.

The nozzles described above may be manufactured by different methods. In one embodiment, the nozzle is injection molded. An inflation bridge may be supported in a lateral channel provided for that purpose. A medial wall may be injection molded or subsequently added. In another embodiment, a nozzle is injection molded without lateral or anterior orifices which are subsequently added, for example laser or water drilled and cut on the walls of the nozzle. In another embodiment, the anterior opening comprises a narrow longitudinal slot cut onto the anterior wall of the body of the nozzle. The slot resembles the vocal cords. When the nozzle is strained, the slot opens allowing a device such as an endotracheal tube to pass through it. In a further embodiment, a high open area insert piece is inserted into the nozzle to provide a medial wall, or ramp, to guide the device. In another embodiment, the insert piece comprises a soft material easily dorsoflexed upon application of force. A plurality of through-holes may be made to provide ventilation through the insert piece.

While the invention has been described as having exemplary designs, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

The invention claimed is:

1. A laryngeal tube comprising:
   a tubular member having a first lumen for receiving gases and delivering the gases to a patient;
   a nozzle having a body portion attached to the tubular member and a tip portion extending from the body portion, the body portion including
   a central cavity,
   an anterior opening having an anterior opening distal edge and being in fluid communication with the central cavity and adapted to receive therethrough a medical component inserted through the first lumen and the central cavity,
   a tongue having a tongue distal end and extending at least-partially over the central cavity, wherein the tongue is configured to block entry of the epiglottis into the central cavity and to deflect anteriorly to allow passage of the medical component through the anterior opening, and wherein when the nozzle is dorsoflexed during normal use at least 10 degrees the tongue distal end moves toward, without reaching or extending over, the anterior opening distal edge, and
   a guide component located in the central cavity, the guide component including an angled surface configured to guide the medical component through the central cavity toward the anterior opening, wherein the guide component comprises a medial wall having a biasing feature causing the medial wall to bulge toward a biasing side of the medial wall when the nozzle is dorsoflexed; and
   a fluid barrier supported by the tip portion and configured to block the oesophagus of the patient.

2. A laryngeal tube as in claim 1, wherein when the nozzle is in an unstrained condition, a distance between the tongue distal end and the anterior opening distal edge ranges between 1 and 25 millimeters.

3. A laryngeal tube as in claim 1, wherein the tongue has a tongue length and the anterior opening has an anterior opening length which is at least 25% longer than the tongue length.

4. A laryngeal tube as in claim 1, wherein the nozzle comprises a ventilation passageway on at least one side of the medial wall.

5. A laryngeal tube as in claim 1, wherein the guide component comprises an insert.

6. A laryngeal tube as in claim 5, wherein the insert is porous to enhance ventilation.

7. A laryngeal tube as in claim 1, further including a proximal service port supported by the tubular member; a service lumen fluidly coupled to the proximal service port; and a distal service port fluidly coupled to the service lumen and located near the anterior opening, the proximal service port, the service lumen and the distal service port defining a service passageway configured to perform a function associated with the larynx of the patient.

8. A laryngeal tube as in claim 7, wherein the function comprises at least one of delivering a medication, sampling a fluid, and introducing a medical device.

9. A laryngeal tube as in claim 7, wherein the function comprises testing carbon dioxide levels in the larynx.

10. A laryngeal tube as in claim 7, further including a second proximal service port supported by the tubular member; a second service lumen fluidly coupled to the second proximal service port; and a nozzle service port fluidly coupled to the second service lumen and in fluid communication with the oesophagus of the patient.

11. A laryngeal tube as in claim 1, further including:
    a proximal inflation port supported by the tubular member;
    an inflation lumen fluidly coupled to the proximal inflation port;
    a distal inflation port fluidly coupled to the inflation lumen and the fluid barrier to inflate the fluid barrier, wherein the inflation lumen is located within a wall of the tubular member; and
    an inflation bridge supported by the nozzle and fluidly coupling the inflation lumen with the distal inflation port, wherein the inflation bridge is a tube.

12. A laryngeal tube as in claim 1, further comprising a distal inflation port fluidly coupled and configured to inflate the fluid barrier; and an inflation tube attached to and supported by the nozzle, the inflation tube fluidly coupling the proximal inflation port with the distal inflation port.

13. A laryngeal tube comprising:
    a tubular member having a first lumen for receiving gases and delivering the gases to a patient;
    a nozzle having a body portion attached to the tubular member and a tip portion extending from the body portion; and
    a fluid barrier supported by the tip portion to block the oesophagus of the patient,
    the body portion including a central cavity, an anterior opening in fluid communication with the central cavity and adapted to receive therethrough a medical component inserted through the first lumen and the central cavity, a medial wall with an angled surface configured to guide the medical component through the central cavity toward the anterior opening and a biasing feature causing the medial wall to bulge toward a biased side of the medial wall when the nozzle is dorsoflexed.

14. A laryngeal tube as in claim 13, wherein the nozzle comprises a ventilation passageway on at least one side of the medial wall.

15. A laryngeal tube as in claim 14, wherein the medial wall is comprised by an insert.

16. A laryngeal tube as in claim 15, wherein the insert is porous to enhance ventilation.

17. A laryngeal tube as in claim 13, further including a proximal service port supported by the tubular member; a service lumen fluidly coupled to the proximal service port; and a distal service port fluidly coupled to the service lumen and located near the anterior opening, the proximal service port, the service lumen and the distal service port defining a service passageway configured to perform a function associated with the larynx of the patient.

18. A laryngeal tube as in claim 17, wherein the function comprises at least one of delivering a medication, sampling a fluid, and introducing a medical device.

19. A laryngeal tube as in claim 17, wherein the function comprises testing carbon dioxide levels in the larynx.

20. A laryngeal tube as in claim 17, further including:
    a proximal inflation port supported by the tubular member;
    an inflation lumen fluidly coupled to the proximal inflation port;
    a distal inflation port fluidly coupled to the inflation lumen and the fluid barrier and configured to inflate the fluid barrier;
    a second proximal service port supported by the tubular member;

a second service lumen fluidly coupled to the proximal service port; and a nozzle service port fluidly coupled to the second service lumen and in fluid communication with the oesophagus of the patient.

21. A laryngeal tube comprising:

a tubular member having a first lumen for receiving gases and delivering the gases to a patient;

a nozzle having a body portion attached to the tubular member and a tip portion extending from the body portion, the body portion including a central cavity, an anterior opening in fluid communication with the central cavity and adapted to receive therethrough a medical component inserted through the first lumen and the central cavity, a tongue extending at least-partially over the central cavity, wherein the tongue is configured to block entry of the epiglottis into the central cavity and to deflect anteriorly to allow passage of the medical component through the anterior opening, and a guide component located in the central cavity, the guide component including an angled surface configured to guide the medical component through the central cavity toward the anterior opening and the guide component including a medial wall having a biasing feature causing the medial wall to bulge toward a biased side of the medial wall when the nozzle is dorsoflexed; and a fluid barrier supported by the tip portion and configured to block the oesophagus of the patient.

22. A laryngeal tube as in claim 21, wherein the nozzle comprises a ventilation passageway on at least one side thereof.

* * * * *